(12) United States Patent
Wright

(10) Patent No.: US 6,478,728 B1
(45) Date of Patent: Nov. 12, 2002

(54) VACUUM CARDIAC STABILIZER WITH GEOMETRICALLY STABLE POROUS PLUG

(75) Inventor: John T. M. Wright, Denver, CO (US)

(73) Assignee: Genesee Biomedical, Inc., Denver, CO (US)

( * ) Notice: Subject to any disclaimer, the term of this patent is extended or adjusted under 35 U.S.C. 154(b) by 0 days.

(21) Appl. No.: 09/540,832

(22) Filed: Mar. 31, 2000

(51) Int. Cl.⁷ .............................. A61F 2/00; A61B 17/00
(52) U.S. Cl. ................................ 600/37; 606/1
(58) Field of Search ...................... 600/37, 205, 231, 600/229; 128/898; 601/1, 166

(56) References Cited

U.S. PATENT DOCUMENTS

| | | | |
|---|---|---|---|
| 5,727,569 A | * | 3/1998 | Benetti et al. ............... 128/898 |
| 5,782,746 A | * | 7/1998 | Wright ........................ 600/37 |
| 5,885,271 A | * | 3/1999 | Hamilton et al. .............. 606/1 |
| 5,891,017 A | * | 4/1999 | Swindle et al. ............. 600/205 |
| 5,906,607 A | * | 5/1999 | Taylor et al. ................... 606/1 |
| 5,927,284 A | * | 7/1999 | Borst et al. ................. 128/898 |
| 5,947,896 A | * | 9/1999 | Sherts et al. ................ 600/229 |
| 6,015,378 A | * | 1/2000 | Borst et al. ................... 600/37 |
| 6,036,641 A | * | 3/2000 | Taylor et al. ............... 600/231 |

* cited by examiner

*Primary Examiner*—Eric F. Winakur
*Assistant Examiner*—Nikita R Veniaminov
(74) *Attorney, Agent, or Firm*—Swanson & Bratschun LLC (57) ABSTRACT

An improved stabilization device of the type used to stabilize a portion of a beating heart by substantially eliminating movement of a portion of the surface tissue of the heart upon which surgical procedures are to be carried out comprising a housing having an opening that, in use, defines with the heart a vacuum chamber, the opening being closed by a geometrically stable porous plug structure.

55 Claims, 3 Drawing Sheets

VACUUM CARDIAC STABILIZER WITH GEOMETRICALLY STABLE POROUS PLUG

FIELD OF THE INVENTION

This invention relates to cardiac stabilization devices of the type that are used to stabilize a portion of a beating heart by substantially eliminating movement of a portion of the surface tissue of the heart upon which surgical procedures are to be carried out.

BACKGROUND OF THE INVENTION

Coronary bypass surgery is a frequently performed cardiac surgery. Approximately 320,000 patients undergo this procedure each year in the U.S. alone. Coronary artery bypass surgery is a technically delicate procedure, and surgeons routinely sew saphenous vein grafts or internal mammary arteries onto coronary arteries as small as one millimeter in diameter. Microsurgical instruments, optical magnification, very fine sutures and fine needles are all necessary to obtain the required precision. In a large majority of procedures the patient is placed on cardiopulmonary bypass as part of the operative procedure. Following commencement of cardiopulmonary bypass, the heart is arrested by the infusion of a cold cardioplegia solution into the coronary arteries and veins. By these means the surgeon is able to operate on a flaccid and motionless heart.

Cardiopulmonary bypass is an expensive and complicated procedure in terms of drug therapy, personnel, equipment and prolonged operation time. It produces metabolic, hematologic and other disturbances to the patient, as well as requiring that the patient receive anticoagulation therapy during the bypass procedure, and reversal of anticoagulant following the cessation of cardiopulmonary bypass. Because of the residual volume of the cardiopulmonary bypass circuit, and the because the patient is anticoagulated, many patients have to receive blood transfusions during or following open heart surgery. Thus, the use of cardiopulmonary bypass has many drawbacks.

Recently, however, methods and apparatus for performing surgery on the beating heart have greatly reduced the trauma of cardiac bypass and other cardiac surgeries. These methods and apparatus are becoming well-known and widely used.

For example, Borst et. al., U.S. Pat. No. 5,836,311, describe these procedures and some forms of apparatus suitable for use in carrying out these surgeries. Borst et. al., describe method and apparatus for temporarily immobilizing a local area of tissue, specifically method and apparatus for temporarily immobilizing a local area of heart tissue to thereby permit surgery on a coronary vessel in that area without significant deterioration of the pumping function of the beating heart. The local area of heart tissue is immobilized to a degree sufficient to permit minimally invasive or micro-surgery on that area of the heart. The Borst et. al. '311 disclosure features a suction device to accomplish the immobilization. The suction device is coupled to a source of negative pressure. The suction device has a series of suction ports on one surface. Suction through the device causes suction to be maintained at the ports. The device is shaped to conform to the surface of the heart. Thus, when the device is placed on the surface of the heart and suction is created, the suction through the ports engages the surface of the heart. The Borst et. al. suction device is fixed or immobilized to a stationary object, such as an operating table or a sternal or rib retractor. Thus, the local area of the heart near the suction device is temporarily fixed or immobilized relative to the stationary object while suction is maintained. In such a fashion, the coronary artery may be immobilized even though the heart itself is still beating so that a bypass graft may be performed. In addition the suction device may be used in either a conventional, open-chest environment or in a minimally-invasive environment, e.g. endoscopic. Additional disclosures of these methods and devices are found in publications of Borst et. al. and in subsequent Borst et. al. patents, e.g. U.S. Pat. Nos. 5,927,284 and 6,015,378.

Another device of this general type is disclosed in U.S. Pat. Nos. 5,727,569 and 5,906,607 to Benetti et. al. Benetti et. al. disclose A method to minimize the motion of an area of tissue at the outer surface of the beating heart proximate to a coronary artery. The outer surface of the beating heart is contacted with an instrument in an area proximate to a coronary artery. The instrument is comprised of an annular housing having a plurality of suction ports disposed therein and housing is shaped to apply negative pressure at several points about the target area. Means are provided for introducing negative pressure to the suction ports. The position of the instrument is manipulated to rest the plurality of suction ports against the outer surface of the beating heart, and a negative pressure is applied to the beating heart by means for introducing the negative pressure to plurality of suction ports connected at several points over the outer surface of the beating heart. Relative motion of an area of tissue of the beating heart is thereby minimized.

Wright, U.S. Pat. No. 5,782,746, discloses a vacuum actuated device that defines, inter alia, a single vacuum chamber in various configurations, a preferable configuration being a generally U-shaped device. Wright '746 discloses a vacuum chamber that encloses a resilient porous polymer pad therein, but does not disclose the use of a geometrically stable porous plug in the vacuum chamber. Exemplary of the devices of the prior art, the disclosures of U.S. Pat. No. 5,782,746 are incorporated herein to the same extent as if the patent was repeated here.

Later patents to Swindle et. al., U.S. Pat. No. 5,891,017, and to Sherts et. al., U.S. Pat. No. 5,947,896 disclose variations on the types of devices disclosed in the previously mentioned patents.

The present invention constitutes an improvement over the open cup or multiple cup vacuum devices, all of which tend to raise a welt of tissue on the heart and, thus, cause some trauma to the heart.

SUMMARY OF THE INVENTION

The present invention provides a vacuum chamber or plural vacuum chambers which have mounted in the chamber a rigid geometrically stable porous plug of predetermined configuration, which may be, for example, an open cell rigid polymer foam, other rigid foam-like structure, a sintered particle geometrically stable porous plug, or a rigid porous plug formed of fibers or fibrous material. The presently preferred embodiment of the invention utilizes sintered stainless steel, but structures which are geometrically stable and which have sufficient porosity to permit the flow of gas are considered equivalent to porous sintered metal or polymer plugs in the context of this invention. The devices rely on vacuum actuation to enhance the gripping of the geometrically stable porous plug, the geometrically stable porous plug eliminating or minimizing drawing heart tissue into the vacuum cups or chambers. The net result is greater stabilization of the heart and less trauma to the heart tissue.

The present invention is an improved cardiac stabilization device and a method using the same. The invention is an improvement on the type used to stabilize a portion of a beating heart by substantially eliminating movement of a portion of the surface tissue of the heart upon which surgical procedures are to be carried out comprising a housing having an opening that, in use, lies adjacent the heart to define with the heart a vacuum chamber. The improved device further comprises a geometrically stable porous plug structure substantially closing said opening, said geometrically stable porous plug structure having a thickness, said geometrically stable porous plug being porous to air through the thickness thereof. The improved device may also comprise a resilient lip structure surrounding the opening. The geometrically stable porous plug may extend outwardly from the opening in the housing, be recessed inwardly from the opening in the housing or be flush with the opening in the housing.

The invention is also embodied as an improvement in the method of performing cardiac surgery that comprises the steps of immobilizing a portion of the heart upon which surgery is to be conducted by attaching by suction force a vacuum chamber that defines a heart engaging opening to In a portion of the surface of the heart, the improvement being the carrying out of the immobilization step with a vacuum chamber that is substantially closed by a geometrically stable porous plug structure secured in the chamber, the geometrically stable porous plug structure having a thickness and being porous to air through the thickness thereof. The method may be carried out using a geometrically stable porous plug structure substantially closing the opening, the geometrically stable porous plug structure having a thickness, the geometrically stable porous plug being porous to air through the thickness thereof. The improved method may also utilize a vacuum chamber that has a resilient lip structure surrounding the opening. The geometrically stable porous plug may comprise open cell foamed polymer. The geometrically stable porous plug may extend outwardly from the opening in the housing, be recessed inwardly from the opening in the housing or be flush with the opening in the housing.

DESCRIPTION OF THE PREFERRED EMBODIMENTS

The embodiments shown herein are preferred but only exemplary as to overall size, shape, etc. Essentially unlimited variation as to the shape of the device is contemplated within the scope of the invention. A great variety of materials may be used. Several examples of material are given but they are not limiting. Any biocompatible materials having the desired physical characteristics can be used.

Figure 1:
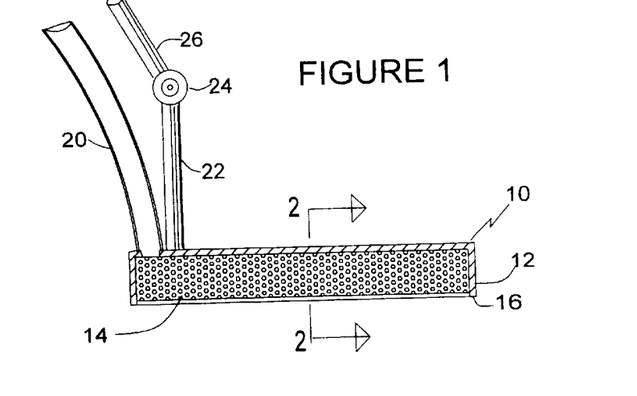
FIG. 1 is a side elevational view largely in cross-section of a preferred embodiment of the device of this invention.
Figure 2:
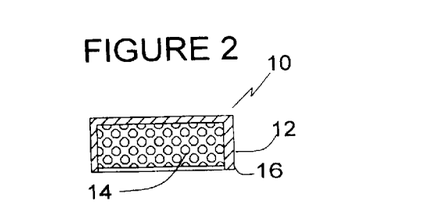
FIG. 2 is a cross-sectional view of the paddle depicted in FIG. 1 taken along lines 2—2 in the direction of the arrows.

Reference is first made to FIGS. 1 and 2 which depict a simple but effective embodiment of the invention that comprises a contacting device, sometimes called a "foot" or a "paddle" 10 which is placed against the surface tissue of a beating heart adjacent the surface area where surgery is to be performed, typically an area proximate to a coronary artery. Means of any type, indicated at 20, for applying suction to the paddle 10 are provided and structure 22, 24 and 26 for positioning the paddle. A tube or cannula connecting the paddle to a vacuum pump or aspirator or any other vacuum source may be used, but any source of vacuum may be used. The structure 22, 24 and 26 comprise two rods connected to each other by means of a ball or pivot joint to permit the paddle to be positioned on the heart in any desired location and orientation. These structures are exemplary only of any of dozens of suction or vacuum devices and supporting devices that may be used without departing from the invention.

Figure 5:
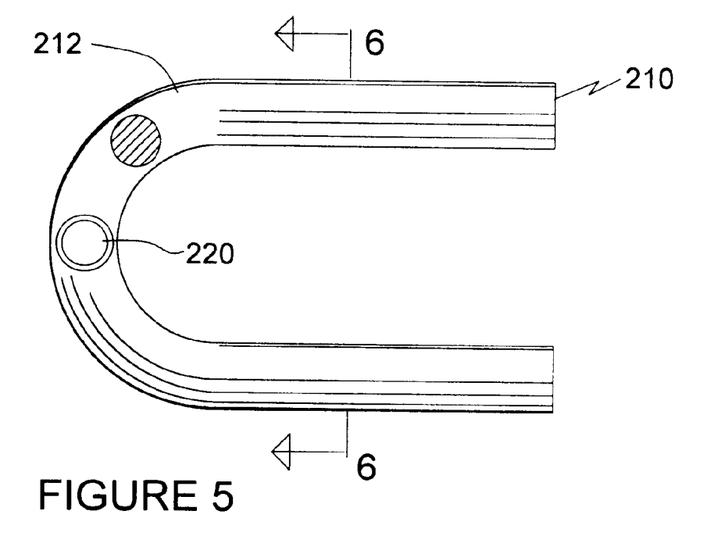
FIG. 5 is a top plan view of a U-shaped device of the type disclosed herein, wherein the open cell porous structure may be of any type and relationship to the chamber.

The paddle 10 in FIG. 1 comprises a housing 12 which is configured and constructed to define a chamber enclosed on all but one side and defining an open side that is configured and adapted to rest against the tissue surface of a beating heart. For simplicity, the paddle in FIG. 1 is shown as a rectangular box enclosed on all but one side by multiple component or a single component enclosing structure. The housing may be made of any conveniently fabricated material. For example, the housing can be made of stamped stainless steel or other metal or of a rigid or semi-rigid polymer. The housing can be made of a polymer that has some flexibility if it is sufficiently rigid not to collapse from the vacuum drawn inside when it is in use. The paddle may be curved to define a generally arcuate tissue engaging structure. The paddle may also be circular, oval, U-shaped or any other shape when viewed in a top plan view. An example of a U-shaped paddle is shown in FIG. 5. Inside the housing, whatever its shape, is positioned a geometrically stable porous plug 14. The preferred plug, presently, is an open cell porous sintered particle plug. The geometrically stable porous plug 14 conforms in size and shape to size and shape of the tissue engaging opening in the housing. In the embodiment shown in FIG. 1, the geometrically stable porous plug is constructed and configured to define a tissue engaging surface lying inside the chamber a slight distance, 0.2 mm to 0.8 mm, typically about 0.5 mm. This is not a critical dimension, however. If the opening is curved, the porous member has same curvature as the opening. In this configuration, a vacuum seal is defined by the housing and the suction is applied to the heart tissue inside the housing through pores in the geometrically stable porous plug, preferably an open cell porous polymer plug. Air or gas is drawn from the chamber by the vacuum means creating a vacuum in the chamber that is transmitted to the heart surface through the porous member. The heart tissue can be drawn into the vacuum chamber only a slight distance, e.g., 0.5 mm, where it will rest against the exterior surface of the geometrically stable porous plug.

The paddle 10 is used in the same general manner as described in the prior art, e.g., the patents of Borst et. al., Benetti et. al. and Wright. The paddle 10 is positioned against the surface of the beating heart adjacent the coronary artery which is to be the subject of the surgery with the geometrically stable porous plug, preferably an open cell geometrically stable porous plug, contacting the surface of the heart. A geometrically stable porous plug is rigid in that it cannot be resiliently deformed in a substantial degree, although it, like all materials, may be sufficiently elastic to bend very slightly under substantial forces. Suction is then applied through tube 20, or any suitable source, to the inside of the chamber defined by the housing 12 and the heart surface. The suction may be created in the chamber by suitable devices, but this approach is considered somewhat cumbersome.

In the preferred embodiment, the plug is relatively firm to rigid and is simply positioned in the housing. It may be secured by adhesive to the walls of the housing for stability in handling. In the preferred embodiment, the open cell porous member is sufficiently porous to permit gas flow through and from all parts of the geometrically stable porous plug to apply vacuum uniformly in the housing to the heart. In use, the heart tissue is drawn into the chamber only a very small distance, e.g. 0.5 mm, by the vacuum applied in the chamber, the edges 16 of which seal to the heart tissue.

Two or more paddles may be used and, once attached, may be moved relative to each other or manipulated to any desired position on the surface tissue of the heart and to present the surgical area for surgery. Surgery is then carried out as in the prior art or using any desired technique.

Sintered stainless steel plugs are presently preferred, but open cell foam may be entirely satisfactory. Open cell biocompatible foams of any desired density and rigidity are well-known. Sheets of such foam of the desired thickness are easily punched to define geometrically stable porous plugs of the same size and shape as the opening in the housing. Open cell foams, or other porous pad structures, formed of any material that is geometrically stable and not an irritant to tissue may be used. Traditional polymers such as acetals, cellulosics, fluorocarbons, nylons, polycarbonates, polystyrenes, polyvinyl chlorides, polyvinyl alcohols, when in fused together to form a geometrically stable porous pad, i.e. a sheet having suitable thickness to provide a form-stable structure, whether of a true open cell foam or of fibers or of another structure that is porous to air through the thickness of the pad may be used. Preferably the pad will be from about 1 mm to about 8 mm in thickness, though thickness is not a critical dimension.

Geometrically stable porous plugs of many types and materials may be used, each material offering a set of advantages and disadvantages. For example, if the paddle configuration is not too complex, a rigid plug made of fused fabric or fibrous material may be suitable. Satisfactory geometrically stable porous plugs can be made in any size, shape and porosity by sintering particles and/or fibers of thermoplastic or heat softenable polymers, e.g., polyolefins., or other materials wherein particles or fibers under pressure and heat bond together at points of contact. Sintered plugs can conveniently be formed in situ in the chamber to fill the chamber, partially or entirely, with a geometrically stable porous plug which, in the sintering operation, may bond to the chamber walls for attachment. It is particularly easy to make porous plugs wherein the porosity in the center area of the plug is greater than the porosity in the peripheral perimeter area of the plug simply by using sintering particles with a smaller average diameter in the peripheral areas than the particles used in the center area of the plug.

Thus, pads formed of material suitable for short term tissue contact that are porous through the thickness of the pad may be used generally interchangeably.

Figure 3:
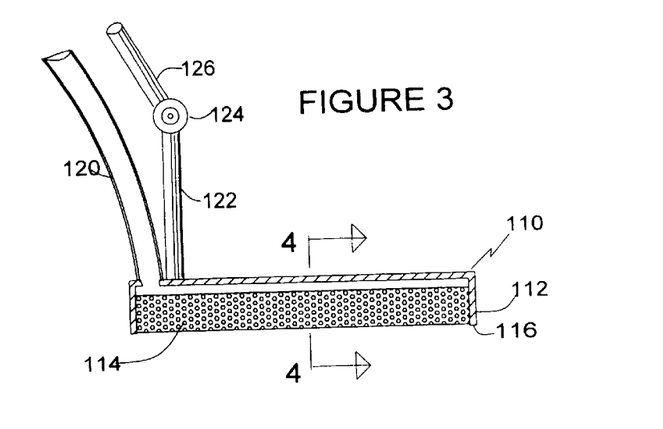
FIG. 3 is a side elevational view largely in cross-section of an alternative embodiment of the device of this invention
Figure 4:
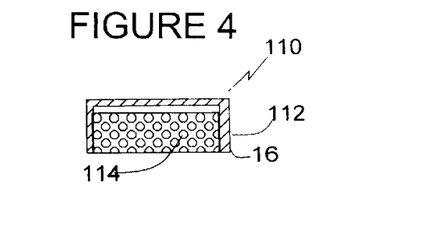
FIG. 4 is a cross-sectional view of the paddle depicted in FIG. 1 taken along lines 3—3 in the direction of the arrows.

The device of FIGS. 3 and 4 is similar to the device of FIG. 1 except for a different construction of the paddle. The paddle 110 is identical to paddle shown in FIG. 1, except that: (a) the pad 114 is coextensive with the lip 116 the opening defined by the housing 112 and (b) the top of the geometrically stable porous plug 114 is configured, constructed and mounted to leave a slight space, e.g. 0.2 mm, between the top of the housing and the geometrically stable porous plug. Vacuum is applied through conduit 120 to the chamber. Positioning structure may be secured to the housing, such as, for example the rods and joints identified at 122, 124 and 126. The space above the geometrically stable porous plug is not usually required, but may be useful with plugs of low porosity.

Reference is now made to FIG. 5. The paddle 210 formed of a housing 212 and connected to a vacuum source 220 and a positioning structure 222 is a generally U-shaped structure. In cross-section, at any point along the length of the housing, the structure may correspond to any plug and housing configuration such as those described hereinbefore and hereinafter. This figure is provided to illustrate the concept that the paddle may be made in any shape—circular, oval, U-shaped, L-shaped, T-shaped, etc.

Figure 6:
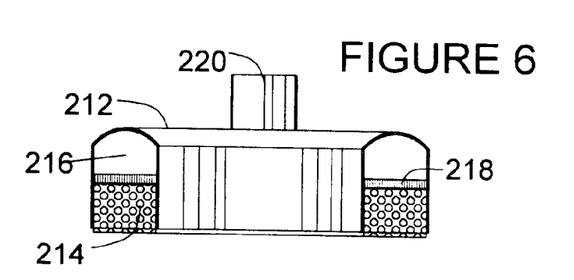
FIG. 6 is a cross-sectional view in enlarged detail taken along a line corresponding to line 6—6 in the direction of the arrows of FIG. 5 depiction one of the optional constructions of the invention.

For convenience, reference is made to FIG. 6 which is one example of the cross-section construction of the device depicted in FIG. 5. The geometrically stable porous plug 214 extends-slightly outside, beyond the edges of the housing 112 that define the heart surface engaging opening. The geometrically stable porous plug extends out of the opening in the housing a very short distance, e.g. 0.2 to 0.8 mm. This extension distance is not considered to be critical and optimization is a simple matter. As discussed, the geometrically stable porous plug is formed of any material suitable for short term tissue contact that is porous through the thickness of the geometrically stable porous plug. The vacuum efficiency of a device such as shown in FIG. 6 is slightly less than the vacuum efficiency of the device shown in FIGS. 1 and 3. FIG. 6 depicts one of the options available in the present invention. If desired, a distinct vacuum chamber 216 may defined in the main vacuum chamber defined by the housing by a porous rigid divider 218 for more equally applying the vacuum through the geometrically stable porous plug.

An advantage of this invention is that with the plug filling the heart-contacting portion of the paddle, the heart tissue is not pulled into the chamber thereby forming a welt on the heart. While resilient foam pads reduce this trauma some, the use of resilient foam pads in chamber may not be adequate to prevent substantial trauma to the heart. Also, there is less danger of injury to the heart tissue by the edges of the housing. In the present embodiment of the invention, vacuum is applied in a myriad of points to the heart tissue with little or no trauma to the heart. Also, the gripping action of the geometrically stable porous plug, especially of certain open cell polymers, may increase the strength of the grip of the tissue and provide better stabilization. All of these advantages are accomplished with devices of the type shown in FIG. 6. In addition, with the geometrically stable porous plug extended outside the tissue contacting opening, the edges of the housing do not contact or barely contact the heart surface. With proper selection of the extension, any loss in vacuum efficiency can be compensated for by widening or enlarging the surface area. Furthermore, if desired, the geometrically stable porous plug can be configured and constructed to permit a vacuum attachment can that can be maintained while drawing blood or fluid away from the surgical area through the geometrically stable porous plug.

Figure 7:
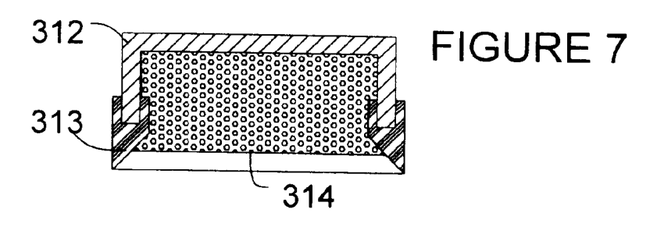
FIG. 7 depicts and end cross-sectional view of an alternative embodiment similar to the embodiment of FIG. 1 but with a resilient flare forming the lower, heart tissue contacting lip of the opening in the housing.

FIG. 7 depicts yet another alternative embodiment of the invention. FIG. 7 is a cross-section corresponding to the cross-section depicted in FIGS. 2 and 4 which, of course, may be in any shape or size. Vacuum efficiency may be improved, according to this embodiment, without risk of heart tissue trauma by adding a resilient lip to define the opening in the housing. The paddle comprises rigid or semirigid wall structures 312 having a suitable vacuum source and positioning secured there to. A resilient lip 313 surrounds the opening and defines the heart tissue contacting surface. The resilient lip may be made of natural or synthetic rubber or any other material that is relatively softer and more resilient than the material of which the housing walls generally are constructed. The geometrically stable porous plug 314 may correspond in shape and position with the edge of the lip 313, may extend slightly beyond the lip or, as shown, be recessed slightly, e.g. 0.2 to 0.8 mm inside the resilient lip. The vacuum produced in the chamber is applied, as in the previously described embodiments, through the geometrically stable porous plug 314. The combination of a geometrically stable porous plug and a resilient lip may provide a good vacuum seal without trauma or likelihood of injury to the heart tissue.

FIGS. 8 through 14 illustrate a slightly different embodiment of the invention in which the bottom of the geometrically stable porous plug and the bottom of the housing, i.e., the lower lip of the housing, lie on a non-planar, usually a generally partial spherical surface. As used here, and as will be apparent from the drawings, the term "bottom" refers to the heart engaging surface of the geometrically stable porous plug and the heart engaging lip of the housing, which are shown at the bottom in the drawings.

Also illustrated in these figures is a geometrically stable porous plug that is in a fixed configuration and made of a rigid porous material. A typical material of this type is a stainless steel frit. Frit filters are, of course, well known. Frits are made of virtually any material that will self bond when the surfaces of two pieces of such material are pressed and/or heated and/or solvent treated. In the case stainless steel, frits are made easily by pressing a body of stainless steel particles together under heat. Open pore frits can be made having virtually any degree of porosity simply by selecting the size and shape particles and the amount of heat and pressure applied. If, for example, 1 millimeter diameter stainless steel spheres are pressed and heated just sufficiently to cause the particles to fuse to each other at the points of contact, a geometrically stable porous plug in which the pores are less than one millimeter in cross-section. In like manner, frits are made by fusing glass beads and beads of various polymers to form a geometrically stable porous plug. If the beads are pressed in a mold, a geometrically stable porous plug conforming to the configuration and shape of the mold will be formed. Stainless steel is a preferred frit material because it forms rigid plugs of fixed configuration which can be machined or pressed into any desired fixed configuration and is biocompatible and relatively inexpensive. Polymer bead frits or even glass frits could be used; however, glass frits may be subject to being broken and, thus, would not be a preferred form of frit.

Stainless steel frits will be referred to as the preferred frit material with the understanding that the exact material of which the frit is made is not important.

Figures 8, 9, 10, 12, 13:
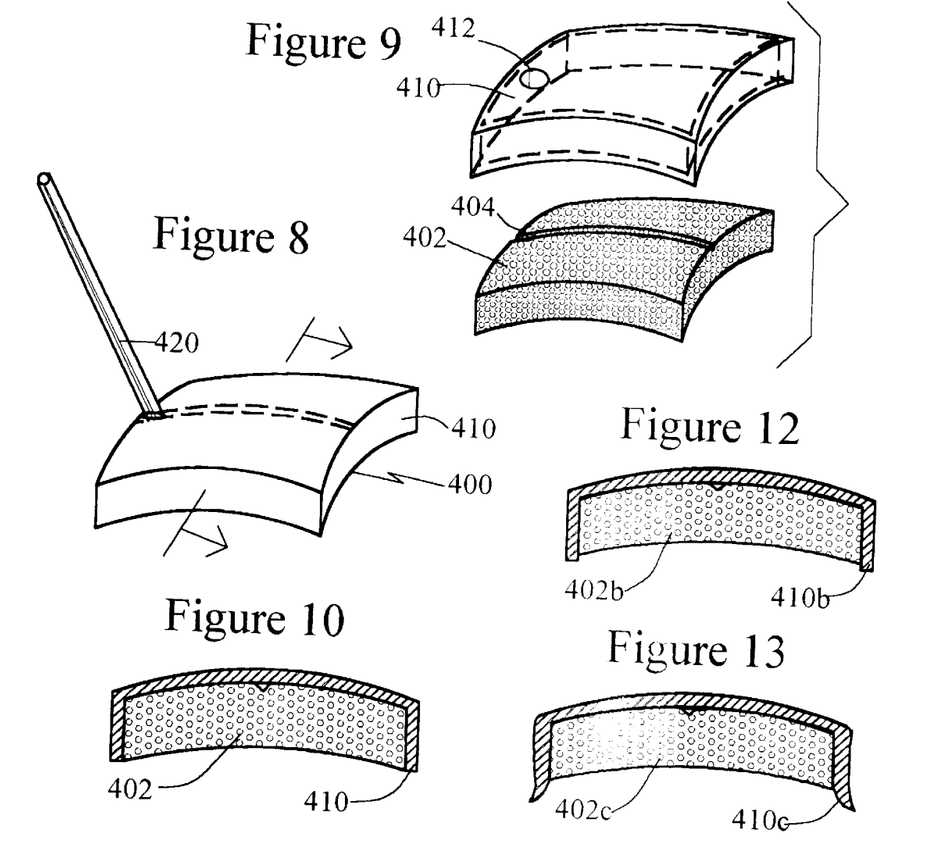
FIG. 8 depicts a variation of the previous embodiments in which the geometrically stable porous plug and housing presenting a non-planar configuration to the surface of the heart and wherein the geometrically stable porous plug is of defined configuration and made of rigid porous material, such as, for example, a stainless steel frit.
FIG. 9 depicts in exploded view the geometrically stable porous plug and housing of the device of FIG. 8.
FIG. 10 depicts, in cross-section taken in the direction of the arrows shown in FIG. 8, a housing and geometrically stable porous plug of the type generally described in relation to FIG. 8 wherein the bottom of the geometrically stable porous plug and the bottom of the housing are contiguous.
FIG. 12 depicts, in cross-section taken in the direction of the arrows shown in FIG. 8, a housing and geometrically stable porous plug of the type generally described in relation to FIG. 8 wherein the bottom of the geometrically stable porous plug extends slightly, e.g. 0.02–0.8 mm outside and the bottom of the housing.
FIG. 13 depicts, in cross-section taken in the direction of the arrows shown in FIG. 8, a housing and geometrically stable porous plug of the type generally described in relation to FIG. 8 wherein the bottom of the housing, and optionally the entire housing, is formed of a flexible material for forming a seal with the heart.

Referring first to FIG. 8, an exemplary cardiac stabilization device 400 comprising a housing 110 inside which is a geometrically stable porous plug to be described to which is attached a rigid or malleable tube. This figure and subsequent figures depict a generally rectangular cardiac stabilization device to simplify the description of the important features of the invention. The device may, of course, be circular, oval, U-shaped, T-shaped, or in any other shape. The device presents a generally hemispherical surface, on the bottom as shown in the drawings, for attachment to the heart. While this is not essential to the invention, as previously described, it is advantageous.

Referring now to FIG. 9 in connection with FIG. 8, it will be seen that the paddle of the cardiac stabilization device comprises a rigid geometrically stable porous plug of fixed configuration 402 which may optionally be configured and constructed to define a gas collection groove 404 in a surface thereof. The housing 410 fits snugly over the plug defining a chamber which is gas-tight except for the gas that enters through the plug. The tube 420, or a solid rod if preferred, may be welded or otherwise attached to the plug extending through the hole 420 in the housing. The tube is sealed to the housing to form a gas tight seal. If, as in a preferred embodiment, a tube is used either to support the plug as shown in FIG. 8, or separately for evacuating the housing to form a partial vacuum inside the housing when the paddle rests upon the beating heart, the tube may be in fluid communication with the groove in the geometrically stable porous plug. The groove may, of course, be of any shape and have any number of segments. While the use of a groove is convenient, it is not necessary.

In use, the paddle is placed on the beating heart in the manner described in the prior art at which time the housing is evacuated and thus becomes a vacuum chamber secured to and stabilizing the surface of the heart. There are considerable advantages in using the rigid geometrically stable porous plug as described. As discussed, the trauma to the heart is greatly reduced and the attachment to the heart is improved. A very significant advantage is the more secure attachment to the heart using a geometrically stable porous plug. Gas must flow from the surface of the heart through the geometrically stable porous plug. There is some inherent pressure drop across the geometrically stable porous plug. Accordingly, even if there is a gas leak at one point adjacent the lip of the housing, vacuum attachment is not lost. Vacuum is still applied to the surface of the heart in the areas slightly distant from the leak in a force equal to the area not effected by the leak times the pressure drop through the geometrically stable porous plug. Plugs with variable pore size, smaller pore size at the edge with larger pore size in the center can be easily manufactured and provide an even greater margin of certainty of attachment.

Quite apparently, the principles of paddle construction described in connection with previously discussed embodiments may be applied to the non-planar, rigid porous block described in the embodiments presently under discussion.

Thus, for example, as shown in FIG. 10, the lower edge of the lip of the housing and the bottom of the edge of the geometrically stable porous plug may be contiguous such that the plug surface and the lip of the housing 410 touch the heart surface at the same time when being attached to the heart.

Figures 11, 14:
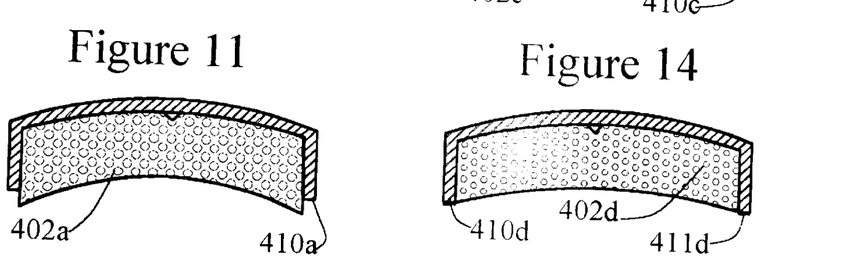
FIG. 11 depicts, in cross-section taken in the direction of the arrows shown in FIG. 8, a housing and geometrically stable porous plug of the type generally described in relation to FIG. 8 wherein the bottom of the geometrically stable porous plug is recessed slightly, e.g. 0.02–0.8 mm inside and the bottom of the housing.
FIG. 14 depicts, in cross-section taken in the direction of the arrows shown in FIG. 8, a housing and geometrically stable porous plug of the type generally described in relation to FIG. 8 wherein the bottom housing is coated with an adhesive for forming a bond to the heart.

As shown in FIG. 11, the lower edge of the geometrically stable porous plug 402a may extend a small amount, e.g., 0.2 mm to 0.5 mm, or more, more distally downwardly, as shown, than the lip of the housing 410a such that only the geometrically stable porous plug is in contact with the heart. The pressure differential across the geometrically stable porous plug owing to flow through the plug assures vacuum attachment of all but the perimeter portion of the geometrically stable porous plug. With a geometrically stable porous plug having gradually decreasing pore size adjacent the edges, produced either during manufacture or by partially plugging the pores or otherwise reducing pore size adjacent the edges after manufacture, a very effective vacuum attachment to the heart can be obtained without exerting the local forces inherently exerted at the lip of the housings in the prior art devices. During manufacture, mixing smaller than average particles with average size particles in the perimeter regions then fusing the frit will produce an excellent frit in which the pressure gradient on the heart is gradual rather than abrupt as is the case in the prior art.

FIG. 12 depicts the variation in which the geometrically stable porous plug is recessed a very small amount, e.g. from 0.2 mm to 0.8 mm, or more, inside the lip of the housing.

FIG. 13 depicts another variation in the configuration of the paddle of the cardiac stabilization device in which at least the lower lip of the housing 410c is flexible or resilient and extends a short distance, e.g., 0.2 mm to 1 mm or more below the geometrically stable porous plug 402c. The extending lip conforms to the surface of the heart and forms a very good vacuum seal with minimal trauma to the heart. The housing may be flexible or resilient in its entirety or may be rigid with flexible or resilient depending lips.

FIG. 14 depicts a slight variation on the device depicted in FIG. 10 wherein a layer of adhesive 411d is placed on the lower edge of the lip of the housing 410d surrounding the geometrically stable porous plug 402d.

It will be perfectly clear from the preceding discussion that the present invention does not depend upon a rigid frit, a stainless steel frit, or any other particular kind of frit. It is known in the filter and structural material arts, in particular, to make frits having virtually any strength, porosity, material that may be desired. Simply for completeness, some consideration of the frits suitable for the present invention are discussed.

Frits made of large, or very large, particles, round or otherwise, could be used. For example, one could use a frit made by pressing and fusing stainless steel spheres or irregular particles having an average particle diameter of up to several millimeters. Such a frit could be machined or fabricated to the desired configuration and used, but it would not be particular desirable. The advantage of a geometrically stable porous plug would not be fully achieved because the pores would be unnecessarily large and the attachment to the heart would be little better than an empty housing or a screened housing would provide.

On the other hand, a frit made of submicron size particles would have a higher than desired pressure drop as air was drawn through it to form a vacuum in the chamber.

While no specific optimum frit has been settled upon, it is believed that frits formed of spherical or at least smooth surface particles of stainless steel, or other material, having a fairly uniform average diameter of from about 0.1 mm up to 1 mm moderately fused together will be most satisfactory.

As an example, it is believed that a frit formed of 0.5 mm stainless steel beads fused together in the shape of the desired paddle or machined to the desired configuration will provide the desired a characteristics. As a further example, a frit in which the center area is formed as just described with the peripheral area, e.g., the outer 1 to 3 mm, being formed of a mixture of 0.2 and 0.5 mm beads is expected to provide a frit that will maintain the vacuum attachment to the heart even if there are some peripheral leaks.

It will also be apparent to those skilled in the art that the housing and the geometrically stable porous plug can be formed of an integral structure simply by closing the pores on the surface of the geometrically stable porous plug or making the pores on the surface so small compared with the pores that principally contact the heart as to provide de minimus flow through the surface comprising, in effect, the housing.

It will be understood from the foregoing discussion and from the Claims appended hereto that within the scope of the invention a very large number of variations and adaptations can be made, especially as to shapes, sizes, dimensions and materials.

Industrial Application

This invention us useful in surgery and in the surgical instrument supply industry.

What is claimed is:

1. In a cardiac stabilization device of the type used to stabilize a portion of a beating heart by substantially eliminating movement of a portion of the surface tissue of the heart upon which a surgical procedures are to be carried out comprising a housing having an opening that, in use, lies adjacent the heart to define with the heart a vacuum chamber; the improvement further comprising a geometrically stable porous plug structure substantially closing the opening, the geometrically stable porous plug structure having a thickness, the geometrically stable porous plug being porous to air through the thickness thereof.

2. The cardiac stabilization device of claim 1 wherein the geometrically stable porous plug comprises open cell foamed polymer.

3. The cardiac stabilizing device of claim 2 wherein the geometrically stable porous plug extends outwardly from the opening in the housing.

4. The cardiac stabilizing device of claim 2 wherein the geometrically stable porous plug is recessed inwardly from the opening in the housing.

5. The cardiac stabilizing device of claim 1 wherein the geometrically stable porous plug extends outwardly from the opening in the housing.

6. The cardiac stabilizing device of claim 1 wherein the geometrically stable porous plug is recessed inwardly from the opening in the housing.

7. In a cardiac stabilization device of the type used to stabilize a portion of a beating heart by substantially eliminating movement of a portion of the surface tissue of the heart upon which surgical procedures are to be carried out comprising a housing having an opening that, in use, lies adjacent the heart to define with the heart a vacuum chamber; the improvement further comprising a resilient lip structure surrounding the opening and a geometrically stable porous plug structure substantially closing said opening, said geometrically stable porous plug structure having a thickness, said geometrically stable porous plug being porous to air through the thickness thereof.

8. The cardiac stabilization device of claim 7 wherein the geometrically stable porous plug comprises open cell foamed polymer.

9. The cardiac stabilizing device of claim 8 wherein the edges of the surface of the geometrically stable porous plug are contiguous with the opening in the housing.

10. The cardiac stabilizing device of claim 9 wherein the geometrically stable porous plug extends outwardly from the opening in the housing.

11. The cardiac stabilizing device of claim 9 wherein the geometrically stable porous plug is recessed inwardly from the opening in the housing.

12. The cardiac stabilizing device of claim 7 wherein the geometrically stable porous plug extends outwardly from the opening in the housing.

13. The cardiac stabilizing device of claim 7 wherein the geometrically stable porous plug is recessed inwardly from the opening in the housing.

14. In the method of performing cardiac surgery comprising the steps of immobilizing a portion of the heart upon which surgery is to be conducted by attaching by suction force a vacuum chamber that defines a heart engaging opening to a portion of the surface of the heart, the improvement wherein the vacuum chamber is substantially closed said heart engaging opening by a geometrically stable porous plug structure secured in said chamber, said geometrically stable porous plug structure having a thickness and being porous to air through the thickness thereof.

15. The method of claim 14 wherein the geometrically stable porous plug comprises open cell foamed polymer.

16. The method of claim 14 wherein the geometrically stable porous plug extends outwardly from the opening in the housing.

17. The method of claim 14 wherein the geometrically stable porous plug is recessed inwardly from the opening in the housing.

18. The method of claim 14 wherein vacuum chamber further comprises a resilient lip structure surrounding the opening therein.

19. The method of claim 18 wherein the geometrically stable porous plug comprises open cell foamed polymer.

20. The method of claim 18 wherein the edge of the geometrically stable porous plug is contiguous with the opening in the housing.

21. The method of claim 18 wherein the geometrically stable porous plug extends outwardly from the opening in the housing.

22. The method of claim 14 wherein the geometrically stable porous plug is recessed inwardly from the opening in the housing.

23. In a cardiac stabilization device of the type used stabilize a portion of a beating heart by substantially eliminating movement of a portion of the surface tissue of the heart upon which surgical procedures are to be carried out comprising a housing having an opening that, in use, lies adjacent the heart to define with the heart a vacuum chamber; the improvement further comprising a rigid geometrically stable porous plug in the housing configured and constructed to form a predefined size and shape structure substantially closing the opening, the geometrically stable porous plug structure having a thickness, the geometrically stable porous plug being porous to air through the thickness thereof.

24. The cardiac stabilization device of claim 23 wherein the geometrically stable porous plug comprises a frit.

25. The cardiac stabilization device of claim 23 wherein the geometrically stable porous plug comprises a stainless steel frit.

26. The cardiac stabilization device of claim 25 wherein the frit comprises stainless steel beads of from 0.1 mm to 2 mm in diameter fused together.

27. The cardiac stabilization device of claim 23 wherein the surface of the geometrically stable porous plug that in use lies adjacent the surface of the heart is generally arcuate in at least one direction.

28. The cardiac stabilization device of claim 27 wherein the geometrically stable porous plug comprises a frit.

29. The cardiac stabilization device of claim 27 wherein the geometrically stable porous plug comprises a stainless steel frit.

30. The cardiac stabilization device of claim 29 wherein the frit comprises stainless steel beads of from 0.1 mm to 2 mm in diameter fused together.

31. The cardiac stabilization device of claim 29 wherein the frit comprises stainless steel beads of from 0.1 mm to 2 mm in diameter fused together.

32. The cardiac stabilization device of claim 23 wherein the geometrically stable porous plug structure is a frit comprising beads of from 0.1 mm to 2 mm in diameter fused together.

33. The cardiac stabilizing device of claim 23 wherein the geometrically stable porous plug extends outwardly from the opening in the housing.

34. The cardiac stabilizing device of claim 23 wherein the geometrically stable porous plug is recessed inwardly from the opening in the housing, and wherein the lip defining the opening in the housing is flexible.

35. The cardiac stabilization device of claim 23 wherein the geometrically stable porous plug comprises a frit having a center portion substantially surrounded by a peripheral portion and wherein the frit has a higher porosity in the center portion than in the peripheral portion.

36. The cardiac stabilization device of claim 35 wherein the geometrically stable porous plug comprises a stainless steel frit.

37. The cardiac stabilization device of claim 35 wherein the frit comprises beads of from 0.1 mm to 2 mm in diameter fused together.

38. The cardiac stabilization device of claim 37 wherein the geometrically stable porous plug comprises a frit having a center portion substantially surrounded by a peripheral portion and wherein the frit has a higher porosity in the center portion than in the peripheral portion.

39. The cardiac stabilization device of claim 35 wherein the housing comprises a non-porous or substantially less porous outer surface of the plug.

40. In the method of performing cardiac surgery comprising the steps of immobilizing a portion of the heart upon which surgery is to be conducted by attaching by suction force a vacuum chamber that defines a heart engaging opening to a portion of the surface of the heart, the improvement wherein the vacuum chamber is substantially closed said heart engaging opening by a rigid geometrically stable porous plug constructed to define a fixed configuration structure in said chamber, said geometrically stable porous plug structure having a thickness and being porous to air through the thickness thereof.

41. The method of claim 40 wherein the geometrically stable porous plug comprises a frit.

42. The method of claim 40 wherein the geometrically stable porous plug comprises a stainless steel frit.

43. The method of claim 42 wherein the frit comprises stainless steel beads of from 0.1 mm to 2 mm in diameter fused together.

44. The method of claim 40 wherein the surface of the geometrically stable porous plug that in use lies adjacent the surface of the heart is generally arcuate in at least one direction.

45. The method of claim 44 wherein the geometrically stable porous plug comprises a frit.

46. The method of claim 44 wherein the geometrically stable porous plug comprises a stainless steel frit.

47. The method of claim 46 wherein the frit comprises stainless steel beads of from 0.1 mm to 2 mm in diameter fused together.

48. The method of claim 40 wherein the geometrically stable porous plug structure is a frit comprising beads of from 0.1 mm to 2 mm in diameter fused together.

49. The cardiac stabilizing device of claim 40 wherein the geometrically stable porous plug extends outwardly from the opening in the housing.

50. The cardiac stabilizing device of claim 40 wherein the geometrically stable porous plug is recessed inwardly from the opening in the housing, the cardiac stabilizing device further comprising a lip defining the opening of the housing, the lip being flexible.

51. The method of claim 40 wherein the geometrically stable porous plug comprises a frit having a center portion substantially surrounded by a peripheral port and wherein the frit has a higher porosity in the center portion than in the peripheral portion.

52. The method of claim 51 wherein the geometrically stable porous plug comprises a stainless steel frit.

53. The method of claim 52 wherein the frit comprises stainless steel beads of from 0.1 mm to 2 mm in diameter fused together.

54. The method of claim 51 wherein the frit comprises beads of from 0.1 mm to 2 mm in diameter fused together.

55. The method of claim 40 wherein the housing comprises a non-porous or substantially less porous outer surface of the plug.

* * * * *